United States Patent [19]

Sauter et al.

[11] 4,456,608

[45] Jun. 26, 1984

[54] AZOLE COMPOUNDS, THEIR PREPARATION, AND FUNGICIDES WHICH CONTAIN THESE COMPOUNDS

[75] Inventors: Hubert Sauter, Mannheim; Eberhard Ammermann, Ludwigshafen; Costin Rentzea, Heidelberg; Ernst-Heinrich Pommer, Limburgerhof, all of Fed. Rep. of Germany

[73] Assignee: BASF Aktiengesellschaft, Fed. Rep. of Germany

[21] Appl. No.: 393,763

[22] Filed: Jun. 30, 1982

[30] Foreign Application Priority Data

Jul. 2, 1981 [DE] Fed. Rep. of Germany ....... 3126022

[51] Int. Cl.³ ............... A01N 43/50; A01N 43/64; C07D 233/60; C07D 249/08
[52] U.S. Cl. ................... 424/269; 424/245; 424/273 R; 548/101; 548/262; 548/341
[58] Field of Search ............ 548/101, 262, 341; 424/245, 269, 273 R

[56] References Cited

U.S. PATENT DOCUMENTS

| | | | |
|---|---|---|---|
| 3,952,002 | 4/1976 | Kramer et al. | 548/262 |
| 4,380,545 | 4/1983 | Kraatz et al. | 548/262 |
| 4,380,546 | 4/1983 | Sauter et al. | 548/262 |

FOREIGN PATENT DOCUMENTS

| | | |
|---|---|---|
| 40350 | 11/1981 | European Pat. Off. . |
| 2918801 | 11/1980 | Fed. Rep. of Germany ...... 424/269 |
| 2926280 | 1/1981 | Fed. Rep. of Germany ...... 548/341 |
| 1318590 | 5/1973 | United Kingdom . |
| 1535777 | 12/1978 | United Kingdom . |

*Primary Examiner*—Alton D. Rollins
*Attorney, Agent, or Firm*—Keil & Weinkauf

[57] ABSTRACT

Azole compounds of the formula

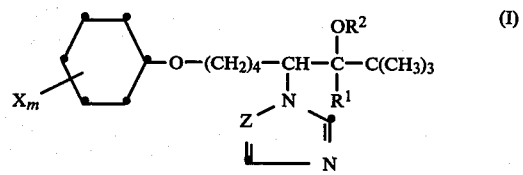

where X is hydrogen, halogen or trifluoromethyl, m is an integer from 1 to 5, Z is N or CH, $R^1$ is $C_2$–$C_4$-alkenyl or $C_2$–$C_4$-alkynyl, and $R^2$ is hydrogen, $C_1$–$C_4$-alkyl, $C_2$–$C_4$-alkenyl, $C_2$–$C_4$-alkynyl or $C_2$–$C_4$-alkanoyl, and their crop-tolerated addition salts with acids, and metal complexes, as well as fungicides which contain these compounds.

2 Claims, No Drawings

AZOLE COMPOUNDS, THEIR PREPARATION, AND FUNGICIDES WHICH CONTAIN THESE COMPOUNDS

The present invention relates to novel, useful azole compounds, processes for their preparation, fungicides which contain these compounds, and the use of these fungicides.

The good fungicidal activity of imidazole derivatives, for example 1-[2-(2,4-dichlorophenyl)-2-(2-propenyloxy)-ethyl]-1H-imidazole (British Patent No. 1,318,590), and of triazole derivatives, for example 2,2-dimethyl-4-(1,2,4-triazol-1-yl)-5-phenylpentan-3-one (German Laid-Open Application DOS No. 2,638,470), has been disclosed. However, when low amounts and low concentrations are used, the effect is not always satisfactory. Furthermore, the fungitoxic action is often associated with high phytotoxicity, so that at the concentrations required for control of fungi in crop protection, for example for the control of rust fungi, the crop plants are also damaged. For these reasons, the compounds are not always suitable for use as crop protection agents for controlling fungi, nor are they suitable for use with all types of crops.

We have found that azole compounds of the formula I

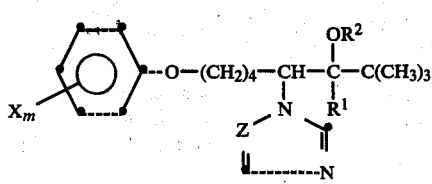

where X is hydrogen, halogen or trifluoromethyl, m is an integer from 1 to 5, and, if m is greater than 1, the X's can be identical or different, Z is N or CH, $R^1$ is $C_2$–$C_4$-alkenyl or $C_2$–$C_4$-alkynyl, and $R^2$ is hydrogen, $C_1$–$C_4$-alkyl, $C_2$–$C_4$-alkenyl, $C_2$–$C_4$-alkynyl or $C_2$–$C_4$-alkanoyl, and their crop-tolerated addition salts with acids, and metal complexes, exhibit a very good fungicidal action coupled with excellent toleration by crops.

In the compounds of the formula I, the azolyl-substituted carbon atom and the adjacent, oxygen-substituted carbon atom are chiral atoms; accordingly, the products are obtained in principle as enantiomer mixtures, which can be separated into the optically active components. Owing to the presence of two chiral centers, the products are also obtained in general as diastereomer mixtures, which can be separated into the individual components in a conventional manner, for example by crystallization or chromatography. However, if the novel compounds are used as fungicides, separation of the enantiomers or diastereomers is normally not necessary. The invention embraces the mixtures as well as the optically active individual substances.

Examples of possible meanings of $X_m$ on the phenoxy radical are hydrogen, 2-fluoro, 4-fluoro, 2-chloro, 3-chloro, 4-chloro, 4-bromo, 2,4-dichloro, 2,4,6-trichloro, 3,5-dichloro, 3-trifluoromethyl and 4-trifluoromethyl $R^1$ is, for example, vinyl, propen-1-yl, propen-2-yl, propen-3-yl, 2-methylpropen-3-yl, ethynyl or propyn-1-yl.

$R^2$ is, for example, hydrogen, methyl, ethyl, n-propyl, prop-2-en-1-yl, prop-2-yn-1-yl, n-butyl, 2-methyl-prop-2-en-1-yl, acetyl, propionyl, butyryl or isobutyryl.

Examples of suitable addition salts with acids are the chlorides, bromides, sulfates, nitrates, phosphates, oxalates and dodecylbenzenesulfonates. The activity of the salts is attributable to the cation, so that the choice of the anion is immaterial.

Suitable metal complexes are compounds of the formula

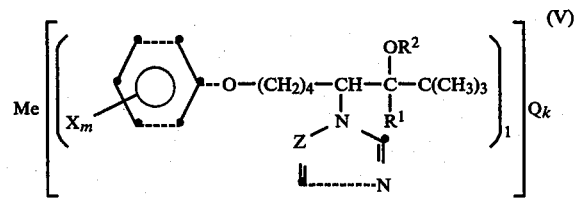

where $X_m$, Z, $R^1$ and $R^2$ have the above meanings, Me is a metal, eg. copper, zinc, tin, manganese, iron, cobalt or nickel, Q is the anion of an inorganic acid, eg. hydrochloric acid, sulfuric acid, phosphoric acid or hydrobromic acid, and l and k are 1, 2, 3 or 4.

The azole compounds of the formula I as claimed in claim 1 are obtained, for example, when a ketone of the formula II

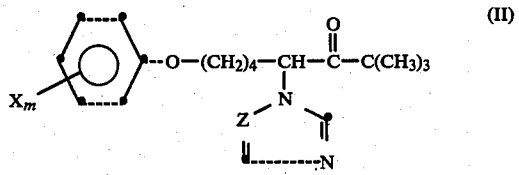

where X, m and Z have the above meanings, is reacted with a Grignard compound of the formula III

where $R^1$ is $C_2$–$C_4$-alkenyl or $C_2$–$C_4$-alkynyl and Hal is chlorine, bromine or iodine, in the presence or absence of a solvent or diluent and in the presence or absence of a magnesium halide or tetraalkylammonium halide, at from 0° to 100° C., and the resulting alcoholate is then hydrolyzed to the tertiary alcohol. Where $R^2$ is not hydrogen, the tertiary alcohol thus obtained is reacted with a $C_2$–$C_4$-alkanoyl chloride or with a $C_2$–$C_4$-alkanoyl anhydride, in the presence or absence of a solvent or diluent, of an inorganic or organic base, and of an acylation catalyst, at from 0° to 100° C. Alternatively, the tertiary alcohol or its alkali metal salt or quaternary ammonium salt can be reacted with an alkylating agent of the formula IV

where $R^2$ is $C_1$–$C_4$-alkyl, $C_2$–$C_4$-alkenyl or $C_2$–$C_4$-alkynyl and L is a nucleophilically displaceable leaving group, in the presence or absence of a solvent or diluent, of an inorganic or organic base, and of a reaction accelerator, at from 0° to 100° C. The various compounds of the formula I which are thus obtained can, if desired, subsequently be converted to their crop-tolerated addition salts with acids, or metal complexes.

The ketones of the formula II which are used as starting materials can be obtained by alkylating a known ketone of the formula VI (German Laid-Open Application DOS No. 2,638,470), or an alkali metal enolate thereof, with an ω-aryloxyalkyl halide VII, in the presence or absence of a base and of a solvent or diluent, to give the ketone of the formula II (cf. Example 1b).

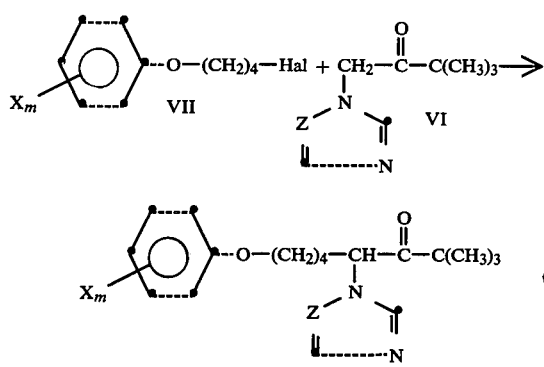

To carry out this reaction, the ketone VI can first be metalized to give the alkali metal enolate, by reacting it, preferably in the presence of a polar aprotic solvent such as dimethylformamide, acetonitrile or tetrahydrofuran, with 0.8–1.2 equivalents, preferably 1.0 equivalent, of a metalizing agent, such as sodium hydride, lithium diisopropylamide or n-butyl-lithium, at 0°–100° C., preferably at 10°–50° C. On subsequent addition of 0.8–2.0, preferably 1.0, equivalents of the particular ω-aryloxybutyl halide of the formula VII, at 0°–100° C., preferably at 5°–30° C., the ketone of the formula II is obtained.

In another embodiment of this process, the ketone VI is reacted with the ω-aryloxybutyl halide VII in the presence of 0.8–1.2 equivalents, preferably 1.0 equivalent, of a base, for example potassium tert.-butoxide, sodium methoxide or potassium hydroxide, the reaction advantageously being carried out in the presence of a solvent or diluent at 0°–100° C., preferably at 5°–50° C.

Suitable solvents or diluents are, once again, polar aprotic solvents, but alcohols, such as methanol or tert.-butanol, can also be used.

The ω-aryloxybutyl halides VII are known compounds or can easily be prepared by conventional methods, for example by monoalkylating a phenol with an aliphatic dihaloalkane, eg. with 1,4-dibromobutane or 1,4-dichlorobutane (cf. Houben-Weyl, Methoden der Organischen Chemie, Volume 6/3, pages 54–59, Thieme-Verlag, Stuttgart, 1965, and Example 1a).

In the process for the preparation of the tertiary alcohols of the formula I, where X, m, Y and R¹ have the above meanings and R² is hydrogen, a ketone of the formula II is reacted with 0.8–2.4 equivalents of a Grignard compound of the formula III R¹—MgHal     III, where R¹ is C₂–C₄-alkenyl or C₂–C₄-alkynyl and Hal is chlorine, bromine or iodine, preferably in the presence of a solvent and in the presence or absence of a salt which increases the yield:

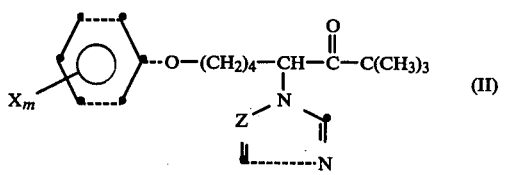

-continued

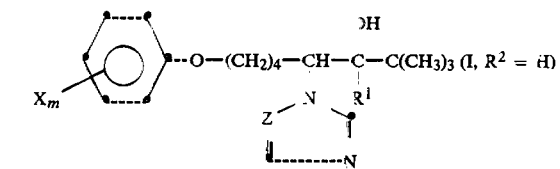

If a solvent is used, it is preferably an ether, eg. diethyl ether, di-n-propyl ether, tetrahydrofuran or anisole, or a tertiary amine, eg. N,N-diethylaniline, or hexamethylphosphoramide; at times, the reaction can also be carried out in a mixture of this solvent with an aliphatic or aromatic hydrocarbon, such as n-hexane or toluene. Salts which increase the yield and which suppress the usual side-reactions are, in particular, anhydrous magnesium halides, eg. anhydrous magnesium bromide, or anhydrous tetraalkylammonium halides, eg. tetra-n-butylammonium chloride. The reaction temperature can be from 0° to 100° C., depending on the solvent, but is preferably from 0° to 60° C. The magnesium alcoholate first formed in the reaction is then converted to the alcohol by hydrolysis with a dilute aqueous acid, eg. hydrochloric acid, sulfuric acid or, preferably, acetic acid, or, in a particularly preferred method, with aqueous ammonium chloride solution; after removal of the aqueous phase, the alcohol can, if desired, be purified in a conventional manner by extraction, recrystallization or chromatography.

In the process for the preparation of the esters of the formula I (R²=C₂–C₄-alkanoyl), the tertiary alcohol of the formula I (R²=H) is reacted with the corresponding acid chloride or acid anhydride, in the presence of an acid acceptor and in the presence or absence of an aprotic solvent or diluent, and preferably in the presence of an acylation catalyst, at from 0° to 100° C., preferably from 10° to 50° C. The acid acceptor, employed in not less than the equivalent amount, can be an inorganic base, eg. sodium amide, or, particularly preferably, pyridine. The acylation catalyst used is advantageously imidazole or 4-dimethylaminopyridine, in an amount of 0.01–0.4 equivalent, unless pyridine is present anyway as a solvent. The solvent employed can be a hydrocarbon, eg. cyclohexane or toluene, an ether, eg. diethyl ether, or an excess of an acid-accepting amine, eg. triethylamine or pyridine.

In the process for the preparation of the ethers of the formula I (R²=C₁–C₄-alkyl, C₂–C₄-alkenyl or C₂–C₄-alkynyl), a tertiary alcohol of the formula I (R²=H), or an alkali metal salt or quaternary ammonium salt thereof, is reacted with an appropriate alkylating agent of the formula IV ti L—R²     IV.

at from 0° to 100° C., in the presence or absence of a solvent or diluent, and in the presence or absence of an inorganic or organic base and of a reaction accelerator.

Examples of the nucleophilically displaceable leaving group L referred to above are halogen, preferably chlorine, bromine or iodine, an alkyl-sulfate group, preferably methyl-sulfate, a substituted or unsubstituted alkylsulfonyloxy radical, preferably methanesulfonyloxy or trifluoromethanesulfonyloxy, and an arylsulfonyloxy radical, preferably a tosylate.

Examples of suitable inorganic or organic bases, which can, where appropriate, also be employed as acid acceptors in the reaction, are alkali metal hydroxides and alkaline earth metal hydroxides, such as sodium hydroxide, potassium hydroxide and calcium hydroxide, alkali metal carbonates, such as potassium carbonate and sodium carbonate, alkali metal hydrides, such as sodium hydride, alkali metal alcoholates and alkaline earth metal alcoholates, such as sodium methylate, magnesium methylate and sodium isopropylate, and tertiary amines, such as trimethylamine, triethylamine, N,N-dimethylaniline, N,N-dimethylcyclohexylamine, N-methylpiperidine and pyridine. However, other conventional bases can also be used.

It is also possible, using a suitable base, for example an alkali metal hydride, such as sodium hydride, or a lithium alkyl, such as butyl-lithium, or an alkali metal alcoholate or alkaline earth metal alcoholate, such as sodium methylate, first to convert the tertiary alcohol of the formula I ($R^2$=H), in a preliminary reaction, to its alcoholate, and then to carry out the reaction with this product.

The preferred solvents and diluents include halohydrocarbons, eg. methylene chloride, chloroform, 1,2-dichloroethane and chlorobenzene, aliphatic and aromatic hydrocarbons, eg. cyclohexane, petroleum ether, benzene, toluene and xylenes, esters, eg. ethyl acetate, amides, eg. dimethylformamide, nitriles, eg. acetonitrile, sulfoxides, eg. dimethylsulfoxide, ketones, eg. acetone and methyl ethyl ketone, ethers, eg. diethyl ether, tetrahydrofuran and dioxane, and mixtures of the above.

Preferred reaction accelerators are metal halides, eg. potassium iodide, crown ethers, quaternary ammonium compounds, eg. tetrabutylammonium iodide, and acids, as well as combinations of these accelerators.

The reactions are in general carried out at from 0° to 100° C., for from 1 to 60 hours, continuously or batchwise, under atmospheric or superatmospheric pressure.

The conventional methods are followed in order to isolate the novel compounds. In general, the products as obtained do not require additional purification, but they can be purified further by conventional methods, such as recrystallization, extraction, distillation or chromatography.

Where desired, a novel compound of the formula I can also be converted to a salt with an inorganic or organic acid, for example to a salt with hydrochloric acid, hydrobromic acid, nitric acid, oxalic acid, acetic acid, sulfuric acid, phosphoric acid or dodecylbenzenesulfonic acid. The activity of the salts is attributable to the cation, so that the choice of anion is immaterial.

A compound of the formula I can also be converted to a metal complex by conventional methods, for example by reacting the compound with a suitable metal salt, eg. copper(II) chloride, zinc(II) chloride, iron(III) chloride, copper(II) nitrate, manganese(II) chloride or nickel(II) bromide.

The Examples which follow illustrate the preparation of the novel compounds of the formula I:

EXAMPLE 1

(a) Preparation of the intermediate 1-bromo-4-phenoxybutane

A mixture of 329 g of phenol, 484 g of dry potassium carbonate, 756 g of 1,4-dibromobutane and 1,000 ml of cyclopentanone was refluxed for 24 hours, while stirring. The solid constituents were filtered off and the filtrate was then concentrated under reduced pressure; the oily residue was taken up in 1,500 ml of methylene chloride, and the solution was extracted with 10×200 ml of 15% strength by weight aqueous sodium hydroxide solution. The organic phase was then extracted with twice 300 ml of water, dried over magnesium sulfate, filtered, and concentrated under reduced pressure. Distillation of the residue gave, at 92°–98° C./0.4 mbar, 395 g of colorless 1-bromo-3-phenoxybutane, which solidified in the receiver; melting point 33°–36° C.

(b) Preparation of the intermediate 2,2-dimethyl-4-(1,2,4-triazol-1-yl)-8-phenoxyoctan-3-one A solution of 14.3 g of 2,2-dimethyl-4-(1,2,4-triazol-1-yl)-butan-3-one (cf. German Laid-Open Application DOS No. 2,638,470) in 20 ml of dimethylformamide was added dropwise, under a dry nitrogen atmosphere, to a stirred suspension of 2.3 g of sodium hydride in 20 ml of dimethylformamide, the reaction temperature being kept at 20°–30° C. by cooling; the mixture was subsequently stirred for 20 hours at room temperature. A solution of 19.5 g of 1-bromo-4-phenoxybutane in 20 ml of dimethylformamide was then added dropwise at 5°–10° C., with continued stirring, and while cooling with ice. After completion of the addition, stirring was continued for 10 hours at 5°–10° C., after which 200 ml of water were added and the mixture was extracted with twice 100 ml of methylene chloride. The combined organic phases were extracted by shaking with water and dried over magnesium sulfate; removal of the solvent under reduced pressure gave an oil from which, on trituration with 20 ml of diisopropyl ether, 17 g of colorless crystals were precipitated; melting point 59°–62° C.

(c) Preparation of 2,2-dimethyl-3-vinyl-4-(1,2,4-triazol-1-yl)-8-phenoxyoctan-3-ol (Compound No. 1)

A solution of 12.6 g of 2,2-dimethyl-4-(1,2,4-triazol-1-yl)-8-phenoxyoctan-3-one was added dropwise to a solution of 8.7 g of vinyl magnesium chloride in 70 ml of tetrahydrofuran, while stirring. After the weakly exothermic reaction was complete, the mixture was refluxed for a further 5 hours and then cooled. Thereafter, a mixture of 5 ml of water and 5 ml of tetrahydrofuran was added dropwise, while cooling with ice, the reaction mixture was stirred for a further 2 hours at room temperature, the precipitated magnesium salts were then filtered off, and the filtrate was concentrated under reduced pressure. The residue from the filtrate was taken up in 100 ml of dichloromethane, the solution was washed with 100 ml of water and then with 100 ml of saturated ammonium chloride solution, and the organic phase was dried over magnesium sulfate and then concentrated under reduced pressure. 8.0 g of pale yellowish crystals of melting point 66°–69° C. (diastereomer mixture 2:1) crystallized from the residual oil on trituration with diisopropyl ether.

Further examples of the compounds of the formula I, which were prepared by similar procedures, are to be found in the Table below.

| Compound no. | $X_m$ | Z | $R^1$ | $R^2$ | M.p. (°C.) |
|---|---|---|---|---|---|
| 2 | H | N | —CH$_2$—CH=CH$_2$ | H | IR (film): 3250, 2960, 1595, 1490, 1240, 1075 915, 755, 695, 670 cm$^{-1}$ |
| 3 | H | N | -ethynyl | H | 129–132 |
| 4 | H | N | -propinyl-1 | H | 113–115 |
| 5 | H | CH | —CH=CH$_2$ | H | 108–111 |
| 6 | H | CH | —CH$_2$—CH=CH$_2$ | H | IR (film): 3350, 2960, 1595, 1495, 1240, 1135 1010, 915, 750, 685 cm$^{-1}$ |
| 7 | H | CH | -ethynyl | H | 156–158 |
| 8 | H | CH | -propinyl-1 | H | 107–110 |
| 9 | 4-F | N | —CH=CH$_2$ | H | 73–75 |
| 10 | 4-F | N | —CH$_2$—CH=CH$_2$ | H | IR (film): 3350, 2960, 1500, 1200, 1135, 1010, 825, 760, 685, 500 cm$^{-1}$ |
| 11 | 4-F | N | -ethynyl | H | 110–112 |
| 12 | 4-F | N | -propinyl-1 | H | 123–126 |
| 13 | 4-Cl | N | —CH=CH$_2$ | H | IR (film): 3400, 2960, 1595, 1490, 1280, 1250, 1140, 1010, 825, 665 cm$^{-1}$ |
| 14 | 3-CF$_3$ | N | —CH=CH$_2$ | H | IR (film): 3400, 2960, 1590, 14,50, 1325, 1240, 1170, 1130, 790, 700 cm$^{-1}$ |
| 15 | 3-Cl | N | —CH=CH$_2$ | H | IR (film): 3400, 2960, 1595, 1280, 1250, 1230, 1140, 770, 680 cm$^{-1}$ |
| 16 | 2,4-Cl$_2$ | N | —CH=CH$_2$ | H | 86–88 |
| 17 | 2,4-Cl$_2$ | N | -ethynyl | H | 123–125 |

The novel compounds, and their salts and metal complex compounds, have an excellent action on a broad spectrum of plant-pathogenic fungi, especially from the Ascomycetes and Basidiomycetes classes. Some of them have a systemic action and may be used as soil and foliar fungicides.

The fungicidal compounds are of particular interest for combating a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combating the following diseases: Erysiphe graminis in cereals, Erysiphe cichoriacearum in Cucurbitaceae, Podosphaera leucotricha in apples, Uncinula necator in grapes, Erysiphe polygoni in beans, Sphaerotheca pannosa in roses, Puccinia species in cereals, Rhizoctonia solani in cotton, Helminthosphorium species in cereals, Ustilago species in cereals and sugarcane, Botrytis cinerea in grapes, Monilia fructigena in apples, Rhynchosporium secale in cereals, and, particularly, Venturia inaequalis (apple scab).

The compounds are applied by spraying or dusting the plants, or treating the seed with the active ingredients. Application may be effected before or after infection of the plants or seed by the fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure a fine and uniform distribution of the active ingredients. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics. e.g. chlorobenzene, paraffins, e.g. petroleum fractions, alcohols, e.g. methanol and butanol, amines, e.g. ethanolamine, and dimethylformamide and water; carriers, for example natural rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt% of active ingredient.

The application rates depend on the effect desired, and vary from 0.02 to 3 kg of active ingredient per hectare or more.

The novel compounds can also be employed in the protection of materials, inter alia for controlling fungi which destroy timber, such as Coniophora puteana and Polystictus versicolor. The novel active ingredients can also be employed as fungicidal constituents of oily formulations for protecting timber against fungi which have a discoloring action. The timber is treated with such formulations by, for example, impregnation or brushing.

The fungicides and the ready-to-use formulations prepared therefrom, such as solutions, emulsions, suspensions, powders, dusts, pastes or granules are employed in a conventional manner, for example by spraying, atomizing, dusting, broadcasting, dressing or watering.

Examples of such formulations are given below.

I. 90 parts by weight of compound 1 is mixed with 10 parts by weight of N-methyl-alpha-pyrrolidone. A mixture is obtained which is suitable for application in the form of very fine drops.

II. 20 parts by weight of compound 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 5 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound 6 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 8 is well mixed with 3 parts by weight of the sodium salt of diisobutyl-naphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound 9 is intimately mixed with 97 parts by weight of particulate kaolin. A dust is obtained containing 3% by weight of the active ingredient.

VII. 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 5 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be mixed and applied with other active ingredients, e.g., herbicides, insecticides, growth regulators, other fungicides and fertilizers. When mixed with other fungicides, the spectrum of fungicidal action is in many cases increased.

The following list of fungicides, with which the compounds according to the invention may be combined, is intended to illustrate and not to restrict the combination possibilites.

Examples of fungicides which may be combined with the active ingredients according to the invention are as follows:
sulfur
ferric dimethyldithiocarbamate
zinc dimethyldithiocarbamate
manganese ethylenebisdithiocarbamate
zinc ethylenebisthiocarbamate
tetramethylthiuram disulfide
manganese-zinc ethylenediamine-bisdithiocarbamate
zinc-(,N,N'-propylene-bisdithiocarbamate)
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
heterocyclic structures, such as
N-(1,1,2,2-tetrachloroethylthio)-tetrahydrophthalimide
N-trichloromethylthiotetrahydrophthalimide
N-trichloromethylthiophthalimide
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-thiocyanomethylthiobenzothiazole
4-(2-chlorophenylhydrazono)-3-methyl-5-isooxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene
and various substances, such as
dodecylguanidine acetate
3-[2-(3,5-dimethyl-2-oxycyclohexyl)-2-hydroxyethyl]-glutarimide
hexachlorobenzene
N-dichlorofluoromethylthio-N,N'-dimethyl-N-phenylsulfuric acid
diamide
D,L-methyl-N-(2,6-dimethylphenyl)-N-(2-furoyl)-alanate
methyl D,L-N-(2,6-dimethylphenyl)-N-(2-methoxyacetyl)-alanate
diisopropyl 5-nitroisophthalate
2,5-dimethylfuran-3-carboxanilide
2,5-dimethylfuran-3-carboxylic acid cyclohexyl amide
2-cyano-N-[(ethylamino)-carbonyl]-2-(methoxyimino)-acetamide
2-methylbenzoic acid anilide
2-iodobenzoic acid anilide
1-(3,4-dichloroanilino)-1-formylamino-2,2,2-trichloroethane
2,6-dimethyl-N-tridecylmorpholine and its salts
2,6-dimethyl-N-cyclododecylmorpholine and its salts 1-(1',2',4-triazolyl-1')-1-(4'-chlorophenoxy)-3,3-dimfthylbutan-2-one 1-(1',2',4'-triazolyl-1')-1-(4'-chlorophenoxy)-3,3-dimethylbutan-2-ol N-(2,6-dimethylphenyl)-N-chloroacetyl-D,L-2-aminobutyrolactone N-(n-propyl)-N-(2,4,6-trichlorophenoxyethyl)-N'-imidazolylurea.

The following Examples 1 to 5 illustrate the fungicidal action of the novel compounds. The compounds (1-(2'-(2",4"-dichlorophenyl)-2'-(2"-propenyloxy)-ethyl)-1H-imidazole) (A) and 2,2-dimethyl-4-(1,2,4-triazol-1-yl)-5-phenylpentanone-(3) (German Laid-Open DOS No. 2,638,470) (B) were used for comparison purposes.

EXPERIMENT 1

Action on wheat mildew

Leaves of pot-grown wheat seedlings of the "Jubilar" variety were sprayed with aqueous emulsions, the solids of which consisted of 80% (by weight) of active ingredient and 20% of emulsifier (sodium lignin-sulfonate), and dusted, 24 hours after the sprayed-on layer had dried, with spores of wheat mildew (Erysiphe graminis var. tritici). The plants were then placed in a greenhouse at 20° to 22° C. and 75 to 80% relative humidity. The extent of mildew spread was determined after 7 days.

The results show that for instance active ingredients 1, 2, 5, 6, 8, 9, 10, 12, 13, 14 15 and 16, applied for example as 0.025% and 0.006% aqueous sprays, have a better fungicidal action (e.g., 100%) than comparative agent A (e.g., 40%).

EXPERIMENT 2

Action on cucumber mildew

The leaves of pot-grown cucumber seedlings of the "Chinesische Schlange" variety were sprayed at the 2-leaf stage with a spore suspension of cucumber mildew (Erysiphe cichoracearum). After about 20 hours, the plants were sprayed to runoff with aqueous emulsions consisting (dry basis) of 80% of active ingredient and 20% of emulsifier (sodium lignin-sulfonate). After the sprayed-on layer had dried, the plants were set up in the greenhouse at from 20° to 22° C. and a relative humidity of 70 to 80%. To assess the action of the novel compounds, the extent of fungus spread was determined after 21 days.

The results show that for instance active ingredients 1, 2, 3, 5, 6, 7, 8, 9, 10, 11, 12, 13, 14, 15, 16 and 17, applied for example as 0.025% aqueous sprays, have a better fungicidal action (e.g., 100%) than comparative agent B (e.g., 40%).

EXPERIMENT 3

Action on leaf rust of wheat

The leaves of pot-grown wheat seedlings of the "Jubilar" variety were dusted with spores of rust (Puccinia recondita). The pots were then placed in a high humidity (90-95%) chamber at from 20° to 22° C. for 24 hours. During this time, the spores germinated and the germ tubes penetrated into the leaf tissue. The infected plants were then sprayed to run-off with a 0.025 wt% aqueous liquor, the solids comprising 80% of active ingredient and 20% of sodium ligninsulfonate. After the spray coating had dried, the test plants were set up in a greenhouse at from 20° to 22° C. and from 65 to 70% relative humidity. After 8 days, the degree of development of the rust fungi on the leaves was determined.

The results show that for instance active ingredients 1, 2, 5, 6, 8, 9, 10, 13, 14, 15 and 16, applied for example as 0.025% and 0.006% sprays, have a better fungicidal action (e.g., 100%) than comparative agent A (e.g., 20%).

EXPERIMENT 4

Action on Botrytis cinerea in pimientos

Pimiento seedlings of the "Neusiedler Ideal Elite" variety were sprayed, after 4 to 5 leaves were well developed, to runoff with 0.05 wt% aqueous suspensions containing (dry basis) 80% of active ingredient and 20% of sodium ligninsulfonate. After the sprayed-on layer had dried, the plants were sprinkled with a conidial suspension of the fungus Botrytis cinerea, and placed at 22° to 24° C. in a chamber of high humidity to obtain optimum conditions for promoting fungus growth. After 5 days, the disease had spread to such a great extent on the untreated plants that the necroses covered the major portion of the leaves.

The results show that for instance active ingredients 1, 2, 5, 6, 8 and 10, applied as a 0.05% aqueous spray, have a good fungicidal action (e.g., 100%).

EXPERIMENT 5

Action on apple scab

The young leaves of pot-grown apple seedlings of the "Golden Delicious" variety were sprayed to runoff with aqueous spray liquors containing (dry basis) 80% of active ingredient and 20% of emulsifier (sodium ligninsulfonte). After the sprayed-on layer had dried, the plants were sprayed with a spore suspension of apple scab (Venturia inaequalis). The inoculated plants were then placed for 10 days in a climatic chamber at 20° to 22° C. and a relative humidity of 95%. The extent of fungus spread on the leaves was then determined.

The results shows that for instance active ingredients 1 and 2, applied as 0.0075% aqueous sprays, have a good fungicidal action (e.g., 100%).

We claim:

1. An azole compound of the formula

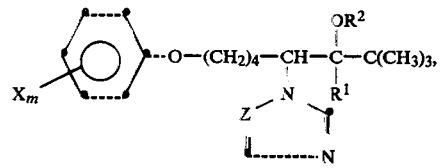

where X is hydrogen, halogen or trifluoromethyl, m is an integer from 1 to 5, and, if m is greater than 1, the X's can be identical or different, Z is N or CH, $R^1$ is $C_2$–$C_4$-alkenyl or $C_2$–$C_4$-alkynyl, and $R^2$ is hydrogen, $C_1$–$C_4$-alkyl, $C_2$–$C_4$-alkenyl, $C_2$–$C_4$-alkynyl or $C_2$–$C_4$-alkanoyl, or a crop-tolerated addition salt with an acid, or a metal complex thereof.

2. A process for combating fungi, wherein the fungi or the objects to be protected against fungus attack are treated with an effective amount of an azole compound of the formula

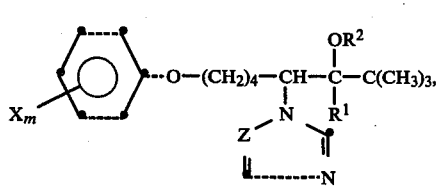
where X is hydrogen, halogen or trifluoromethyl, m is an integer from 1 to 5, and, if m is greater than 1, the X's can be identical or different, Z is N or CH, $R^1$ is $C_2$–$C_4$-alkenyl or $C_2$–$C_4$-alkynyl, and $R^2$ is hydrogen, $C_1$–$C_4$-alkyl, $C_2$–$C_4$-alkenyl, $C_2$–$C_4$-alkynyl or $C_2$–$C_4$-alkanoyl, or a crop-tolerated addition salt with an acid, or a metal complex thereof.
* * * * *